United States Patent [19]

Gates et al.

[11] Patent Number: 5,522,875
[45] Date of Patent: Jun. 4, 1996

[54] MEDICAL ELECTRICAL LEAD SYSTEM HAVING A TORQUE TRANSFER STYLET

[75] Inventors: James T. Gates, Maple Grove; Kenneth B. Stokes, Elk River, both of Minn.

[73] Assignee: Medtronic, Inc., Minneapolis, Minn.

[21] Appl. No.: 282,421

[22] Filed: Jul. 28, 1994

[51] Int. Cl.⁶ .................................................. A61N 1/05
[52] U.S. Cl. ....................... 607/127; 128/772; 607/120; 604/166; 604/282
[58] Field of Search .................... 128/657, 772; 607/122, 126, 127, 120; 604/164–166, 170, 281, 282

[56] References Cited

U.S. PATENT DOCUMENTS

| | | |
|---|---|---|
| 3,476,116 | 11/1969 | Parsonnet et al. . |
| 3,827,428 | 8/1974 | Hon et al. . |
| 3,906,938 | 9/1975 | Fleischhacker . |
| 3,911,928 | 10/1975 | Lagergren . |
| 4,106,512 | 8/1978 | Bisping . |
| 4,146,036 | 3/1979 | Dutcher et al. . |
| 4,217,913 | 8/1980 | Dutcher . |
| 4,236,529 | 12/1980 | Little . |
| 4,311,153 | 1/1982 | Smits . |
| 4,350,169 | 9/1982 | Dutcher et al. . |
| 4,357,946 | 11/1982 | Dutcher et al. . |
| 4,408,604 | 10/1983 | Hirshorn et al. . |
| 4,498,482 | 2/1985 | Williams . |
| 4,649,937 | 3/1987 | DeHaan et al. . |
| 4,760,852 | 8/1988 | Lekholm . |
| 4,796,642 | 1/1989 | Harris . |
| 4,815,478 | 3/1989 | Buchbinder et al. . |
| 4,819,661 | 4/1989 | Heil, Jr. et al. . |
| 4,827,940 | 5/1989 | Mayer et al. . |
| 4,832,047 | 5/1989 | Sepetka et al. ................ 128/772 |
| 4,844,099 | 7/1989 | Skalsky et al. . |
| 4,917,106 | 4/1990 | Olivier . |
| 4,953,564 | 9/1990 | Berthelson . |
| 4,971,490 | 11/1990 | Hawkins ................ 128/772 |
| 4,972,848 | 11/1990 | Di Domenico et al. . |
| 5,002,067 | 3/1991 | Berthelsen et al. . |
| 5,003,992 | 4/1991 | Holleman et al. . |
| 5,014,720 | 5/1991 | Barcel et al. . |
| 5,020,545 | 6/1991 | Soukup ................ 607/127 |
| 5,052,404 | 10/1991 | Hodgson . |
| 5,165,421 | 11/1992 | Fleischhaker et al. . |
| 5,176,149 | 1/1993 | Grenouillet ................ 128/772 |
| 5,211,636 | 5/1993 | Mische . |
| 5,213,111 | 5/1993 | Cook et al. . |
| 5,234,451 | 8/1993 | Osypka . |
| 5,246,014 | 9/1993 | Williams et al. . |
| 5,259,393 | 11/1993 | Corso, Jr. et al. ................ 128/772 |
| 5,259,394 | 11/1993 | Bens . |

OTHER PUBLICATIONS

Medtronic Technical Manual, Myocardial, Unipolar Lead, Mar. 1991, UC9001746bEN 195409–002.

*Primary Examiner*—William E. Kamm
*Assistant Examiner*—Jeffrey R. Jastrzab
*Attorney, Agent, or Firm*—Michael J. Jaro; Harold R. Patton

[57] ABSTRACT

A medical electrical lead system having a torque transfer stylet. In a preferred embodiment, the torque transfer stylet comprises an elongated, stylet wire having proximal, intermediate and distal sections. The proximal and distal section of the stylet wire have a first diameter. The intermediate section spans between the proximal and distal sections. The stylet wire in this region, however, has a second diameter, the second diameter smaller than the first diameter of the proximal and distal sections. In addition, the intermediate section further has a length of torque coil wrapped thereabout. The torque coil preferably is wound in a coiled diameter which is the same as the first diameter of the proximal and distal sections of the stylet wire. Through such a configuration the stylet has an overall nearly uniformed diameter through its length.

30 Claims, 12 Drawing Sheets

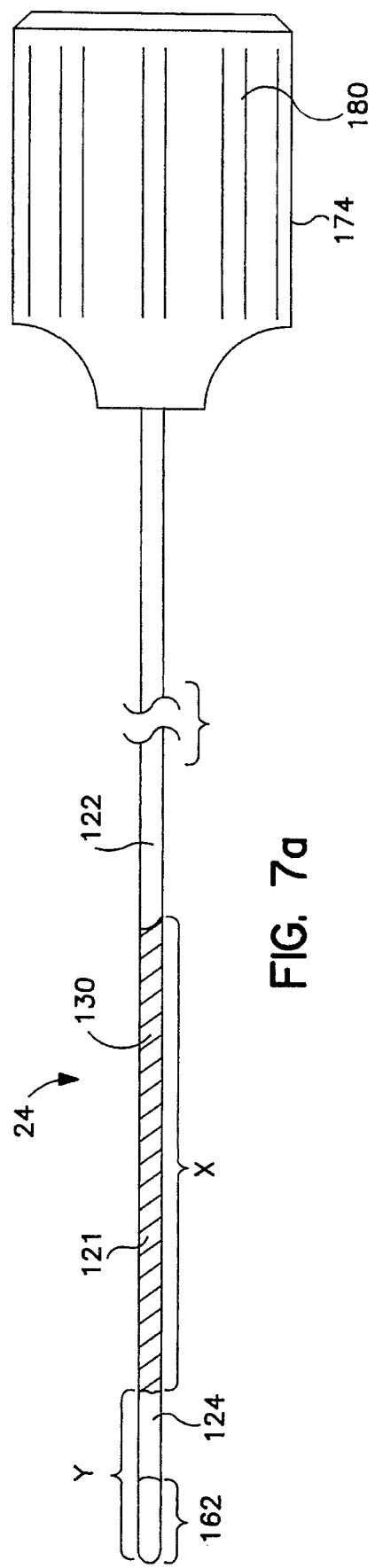
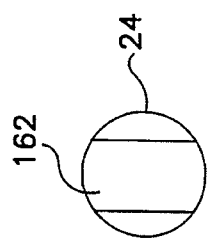
FIG. 7a
FIG. 7b

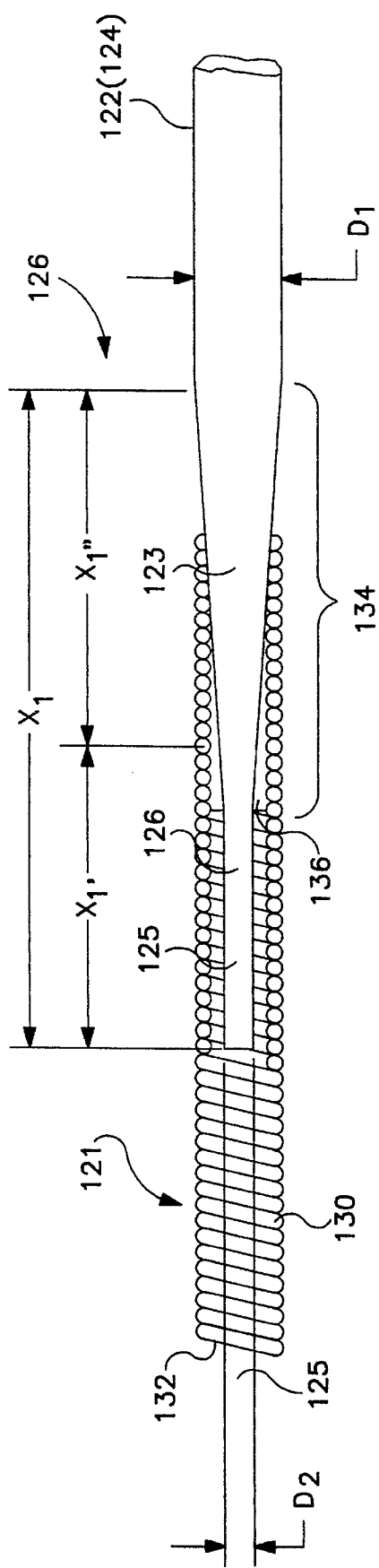
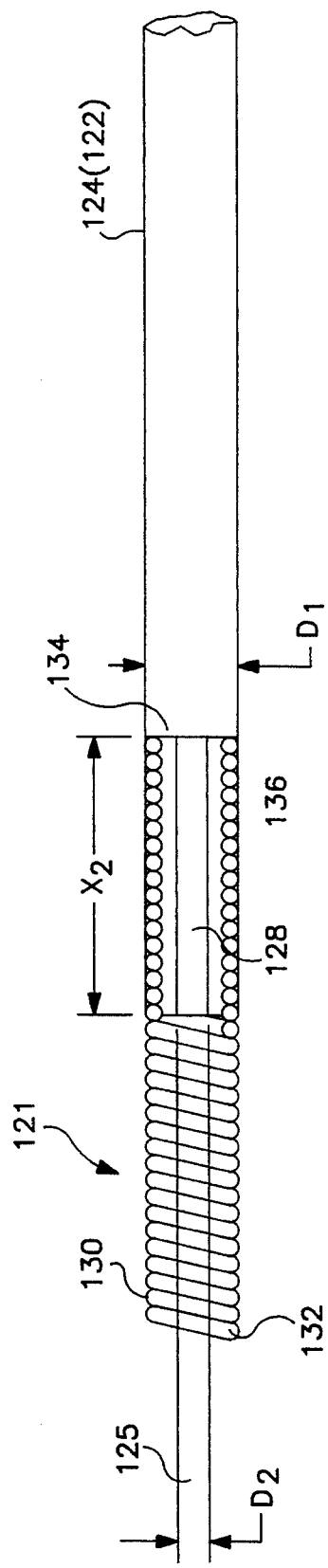
FIG. 9
FIG. 10

MEDICAL ELECTRICAL LEAD SYSTEM HAVING A TORQUE TRANSFER STYLET

REFERENCE TO RELATED APPLICATION

This application is related to the copending application of James T. Gates entitled "MEDICAL LEAD HAVING SEGMENTED ELECTRODE" filed this same day and assigned to the assignee of the present invention.

FIELD OF THE INVENTION

The present invention relates to a medical electrical lead system having a torque transfer stylet for electrically connecting an organ to an electrical device, and particularly to a torque stylet which provides the transmission of rotational torque from a proximal end of the stylet, outside the body, to a distal end of the stylet, inside the body, while the lead and stylet are bent.

BACKGROUND OF THE INVENTION

In the medical field, various types of body implantable leads are known and used. One type of commonly used implantable lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Passive fixation mechanisms, such as a tine assembly, lodge or passively fix the lead to the heart. Active fixation mechanisms use a structure, such as a helix or hook, to engage into or actively fix themselves onto the heart.

A preferred means for introducing an endocardial lead into the heart is through a vein. Specifically, such a lead, called a transvenous lead, is introduced into and maneuvered through the vein so the distal end is positioned within the heart. Introduction of an active fixation lead, however, in such a manner presents difficulties. In particular, an exposed sharpened helix, may damage a vein during introduction. Thus many active fixation leads have helixes which either retract into the lead body or are shielded during introduction. See, for example, U.S. Pat. No. 4,972,848 of the Di Domenico (helix shielded within lead body which may be extended to engage cardiac tissue): U.S. Pat. No. 5,003,992 of Holleman et. al (plunger through helix guards against damage to tissue by the helix, plunger may be retracted to permit helix to engage tissue) and U.S. Pat. No. 4,827,940 of Mayer et. al. (soluble cover shields helix until positioned approximate fixation site.)

Retraction into and extension from the lead body is a preferred method of shielding the helix in a transvenous, endocardial lead. Various means may be used to achieve such retraction and extension. One means used has been with a stylet. For example, U.S. Pat. No. 4,217,913 to Dutcher et al. discloses a lead having a coiled conductor encased within an insulating material. A ridged helix is attached at the distal end of the lead by a piston. The lead body is shaped to permit the introduction of a stylet therethrough. The stylet and piston, in particular, are shaped to mutually engage one another. Specifically, the stylet has a screwdriver shaped distal tip which engages into a slot in the head of the piston. When these two objects are mated together and the stylet is rotated, it transmits rotational torque to the piston. The piston, in turn, rotates the attached helix such that when rotated in the first direction, the helix is advanced out of the distal end of the lead body so it may introduced into endocardial tissue. When rotated in a second direction the helix retracts into the lead body so it disengages endocardial tissue. In various endocardial screw-in lead designs the helix may be either electrically isolated from a spaced electrode or may itself constitute the electrode.

One difficulty sometimes encountered with such a design is when it becomes necessary to bend the lead so the distal end may be positioned in a desired location. This type of bending is often required, for example, when the lead needs to be implanted in the right atrium of the heart. Bending of the lead body may be readily accomplished by various means. Inducing a torque to the distal end while bent, however, presents a challenge. Specifically, because the lead is bent rotation of the proximal end of the stylet will tend to cause the bent stylet and thus bent lead body to rotate thereabout, that is, it will cause the entire bent lead to rotate such that the distal end dislodges from its desired location. It is preferred if rotation of the stylet, even though bent, does not cause the distal end to dislodge, but rather only rotates about its longitudinal axis.

One solution which has been proposed to permit a helix to be rotated at the distal end of a lead by a stylet while the lead and stylet are bent may be seen in the U.S. Pat. No. 4,350,169 to Dutcher et al. As seen, this discloses a stylet having a narrowed or necked region adjacent to the distal end of the stylet. This necked or narrowed section increases the flexibility of the stylet in that region without detracting from the ability of the stylet to transmit torque from its proximal end to its distal end. In particular it was believed that by providing a readily flexible necked or narrowed intermediate section the stylet would bend in conformity with the lead body but would rotate about its longitudinal axis when rotated.

In practice, it has been found, however, that this necked or narrowed section in the stylet still imparts a considerable tendency to straighten the bend or curve in the lead and thus dislodge the tip of the lead from the desired position. In order to offset this straightening tendency, the J-shape of the preformed atrial leads must be made inherently stiffer. This stiffening can cause additional chronic trauma at the implant site which can lead to higher stimulation thresholds or poor sensing or both during chronic use of the lead. These difficulties have slowed wide-spread adoption of transvenous endocardial screw-in leads.

One device used to provide the transmission of torque about a bend is disclosed in U.S. Pat. No. 5,165,421 of Fleischhacker et al. which discloses a hollow lumen cable apparatus. Specifically this apparatus comprises a pair of counter wound coils. These coils permit the apparatus to be highly flexible and pliant while permitting torque to be readily transferred. One drawback with such an apparatus, however, is its flexibility. For lead implantation, although it may be necessary for the lead to bend, it is still necessary for the stylet to provide some degree of stiffness to the lead.

SUMMARY OF THE INVENTION

It is accordingly an object of the present invention to provide a medical electrical lead system having a torque stylet which transmits torque from the proximal end of the stylet to the distal end of the lead while both are bent.

This object of the present invention is accomplished by providing a medical electrical lead system having a torque transfer stylet. In a preferred embodiment, the torque transfer stylet comprises an elongated, stylet wire having proximal, intermediate and distal sections. The proximal and distal section of the stylet wire have a first diameter. The intermediate section spans between the proximal and distal sections. The stylet wire in this region, however, has a second diameter, the second diameter smaller than the first diameter of the proximal and distal sections. In addition, the intermediate section further has a length of torque coil wrapped thereabout. The torque coil preferably is wound in a coiled diameter which is the same as the first diameter of the proximal and distal sections of the stylet wire. Through such a configuration the stylet has an overall nearly uniformed diameter through its length.

BRIEF DESCRIPTION OF THE DRAWINGS

The present invention may be better understood and appreciated with reference to a detailed description of the invention, when read in conjunction with the accompanying drawings, wherein:

FIG. 2b is a greatly enlarged sectional view of a distal portion of the electrode assembly of FIG. 2a;

FIG. 2c is a greatly enlarged sectional view of a proximal portion of the electrode assembly of FIG. 2a;

FIGS. 3a and 3b are front and sectional views, respectively, of a distal tip electrode in the electrode assembly of FIG. 2a;

FIG. 5 is a side view of a helix assembly from the electrode assembly of FIG. 2a;

FIGS. 6a and 6b are rear and sectional views, respectively, of a helix seal in the electrode assembly of FIG. 2a; and FIGS. 7a and 7b are greatly enlarged side and distal end views, respectively, of a stylet used in conjunction with the lead from FIG. 1;

FIG. 9 is an enlarged sectional view of the stylet of FIG. 7 showing the bonding of a proximal end section of the wire torque coil to the proximal straight wire section in the reduced diameter portion thereof;

FIG. 10 is an enlarged sectional view of the stylet of FIG. 7 showing the bonding of the distal end section of the wire torque coil to the distal straight wire section in the reduced diameter portion thereof;

The drawings are not necessarily to scale.

DESCRIPTION OF THE INVENTION

The present invention is described within the context of a screw-in bipolar transvenous endocardial lead adapted for use in connection with an implantable cardiac pulse generator. The present invention, however, may be advantageously practiced in conjunction with many different types of implantable medical devices as well as many other various embodiments of a medical electrical lead besides the particular bipolar lead described herein.

MEDICAL ELECTRICAL LEAD

Figure 1:
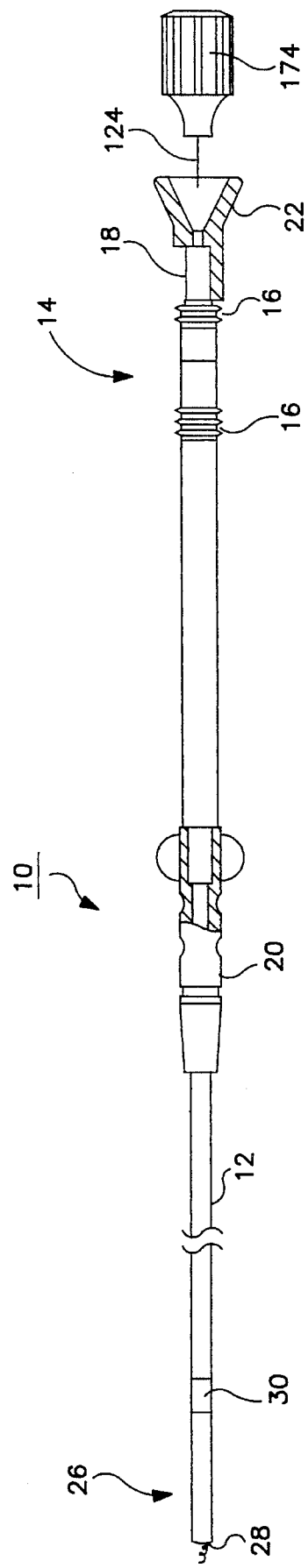
FIG. 1 is a plan view of a stylet-activated, steroid eluting, screw-in endocardial bipolar pacing lead in which the stylet of the present invention may be used.

FIG. 1 is a plan view of a stylet-activated, steroid eluting, screw-in endocardial bipolar pacing lead 10 in which the stylet of the present invention may be used. As seen Lead 10 has a flexible, elongate lead body 12 covered by an insulative sleeve, such as polyurethane or silicone rubber. Terminal assembly 14 is provided at the proximal end for coupling lead 10 to an implantable pulse generator (not shown.) Terminal assembly 14 has sealing rings 16 and terminal pin 18, all of a type known in the art.

An anchoring sleeve 20 (shown partially in cross-section) may also be provided for suturing lead body 12 to body tissue. Anchoring sleeve 20 and terminal assembly 14 are preferably fabricated from silicone rubber, although they may also be constructed of any other suitable biocompatible material known in the art.

Lead 10 also includes stylet guide 22 and torque transfer stylet 24 coupled to terminal pin 18 for imparting stiffness to lead 10 during placement and for actuation of the lead's fixation helix, described below.

With continued reference to FIG. 1, an electrode and fixation assembly designated generally as 26 is disposed at the distal end of lead body 12. Electrode and fixation assembly 26 is, in the disclosed embodiment, of the bipolar type and has tip electrode 28 at its distal end and a ring electrode 30 spaced proximally back from the distal end. Tip electrode 28 and ring electrode 30 are coupled to separate, insulated lead conductors (not shown in FIG. 1) which extend along the length of lead body 12. Lead conductors are preferably configured as concentric multi-filar coils of MP35N or any other suitable biocompatible conductive alloy, such as a platinum-iridium alloy. The concentric coiled design allows for a longitudinal lumen to exist along the length of lead body 12, such that a stylet may be received therein.

Figure 2A:
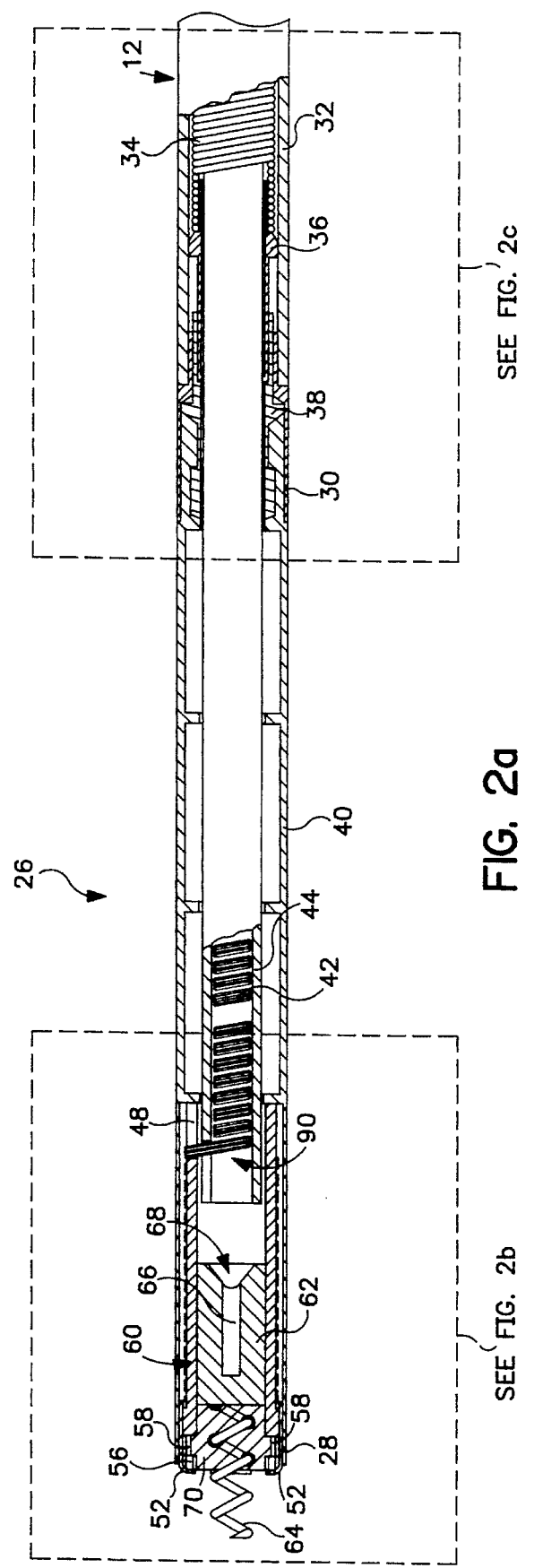
FIG. 2a is a greatly enlarged sectional view of a distal segment of the lead of FIG. 1 including the lead's electrode assembly.
Figure 2B:
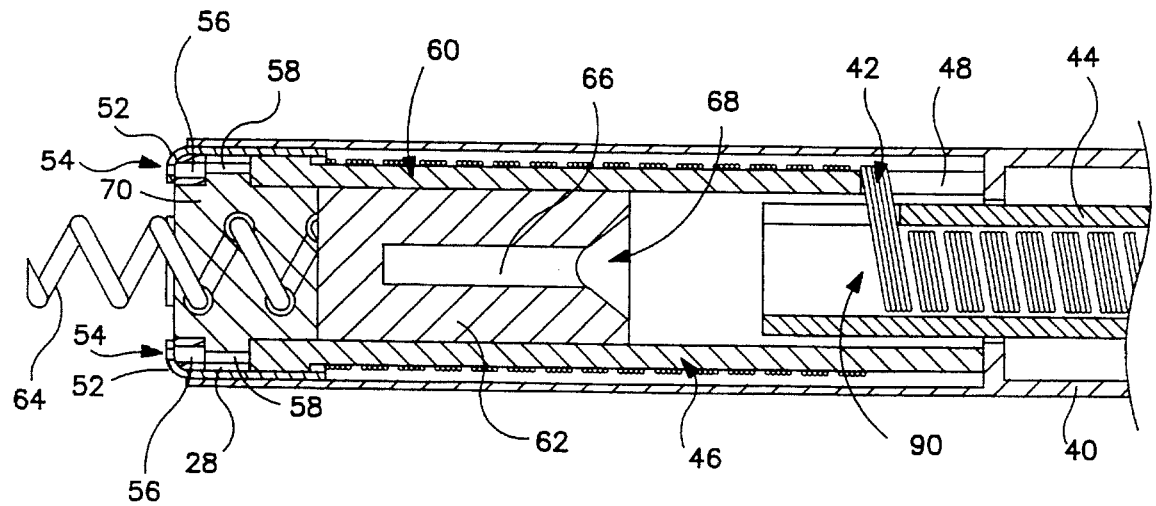

In FIG. 2a, there is shown a greatly enlarged sectional view of a distal portion of lead body 12 and electrode and fixation assembly 26. In FIG. 2b there is shown the portion of FIG. 2a contained within dashed line 2b, and in FIG. 2c there is shown the portion of FIG. 2a contained within dashed line 2c, both even further enlarged for the sake of clarity.

Figure 2C:
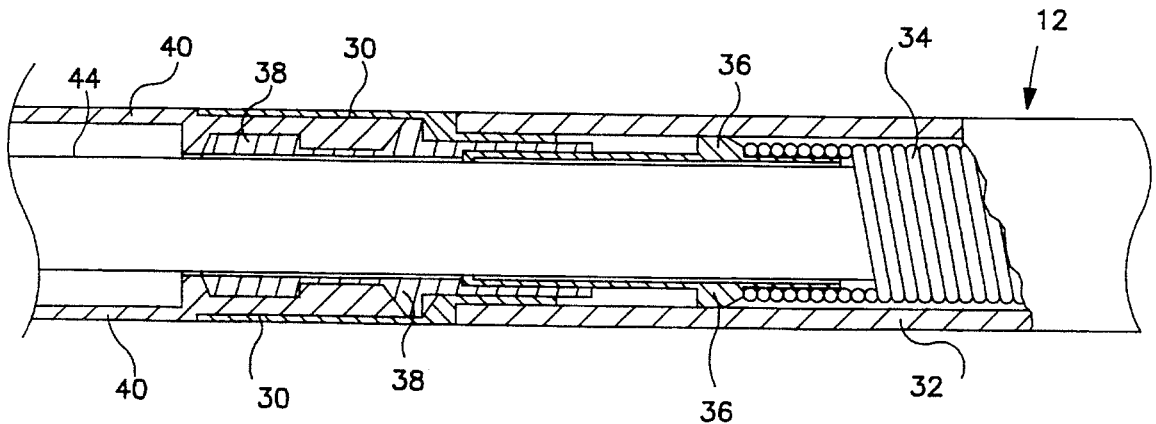

As shown in FIGS. 2a and 2c, lead body 12 has an outer flexible insulative sheath 32 made of silicone rubber, polyurethane, or the like. Outer insulative sheath 32 covers first coiled conductor 34. Conductor 34 extends along through lead body 12 and terminates at its distal end where it is electrically coupled, for example by spot or laser welding, to a crimp sleeve 36 made of stainless steel or the like. Crimp sleeve 36, in turn, is in electrical connection with a sleeve 38 which is similarly made of stainless steel or the like. Sleeve 38 is engaged within and in electrical contact with substantially cylindrical ring electrode 30, which is preferably made of a 90/10 platinum/iridium alloy.

Partially engaged between ring electrode 30 and sleeve 38 is a tip/ring spacer 40, which is preferably made of silicone rubber. In addition to establishing a predetermined distance between ring electrode 30 and tip electrode 28, tip/ring spacer 40 functions to define a substantially cylindrical chamber in which the remaining components are disposed as well as to define the outer surface of electrode and fixation assembly 26. In the disclosed embodiment, tip/ring spacer 40 has dimensions such that a constant lead body diameter is maintained between tip electrode 28 and ring electrode 30.

Figure 4:
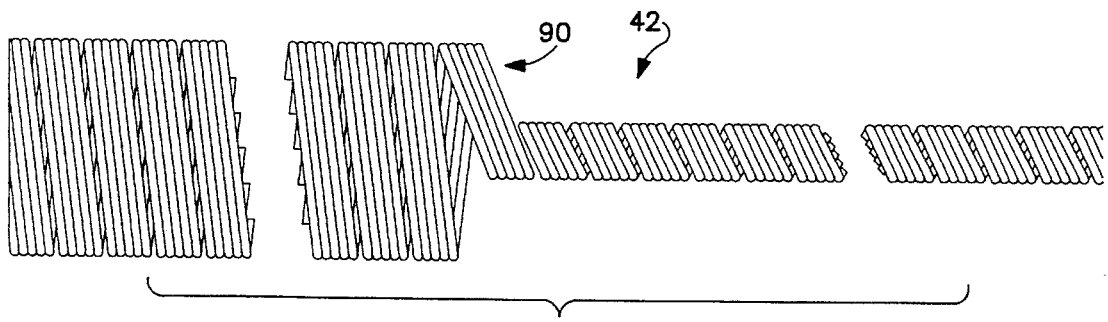
FIG. 4 is a greatly enlarged side view of a coiled conductor within the lead of FIG. 1.

Extending along the length of lead body 12 through crimp sleeve 36, sleeve 38, ring electrode 30, and tip/ring spacer 40 is a second coiled conductor 42, which is insulated from outer coiled conductor 34 by inner insulative sheath 44 which, like outer sheath 32 is made of silicone rubber, polyurethane, or the like. Inner conductor 42 terminates at a substantially cylindrical helix sleeve 46. In the presently preferred embodiment, helix sleeve 46 is made of machined polysulfone, and is provided with a rectangular slot 48 which allows the diameter of the coil defined by inner conductor 42 to increase at a "dog-leg" point designated generally as 90 in FIGS. 2a and 2b. Distally from "dog-leg" point 90, inner conductor 42 coils around the outer surface of helix sleeve 46 toward the distal end of helix sleeve 46, and is electrically coupled, e.g., by spot or laser welding, to tip electrode 28. The configuration of inner conductor 42 and "dog-leg" point 90 are best seen in FIG. 4, which shows conductor 42 in isolation.

Figure 3A:
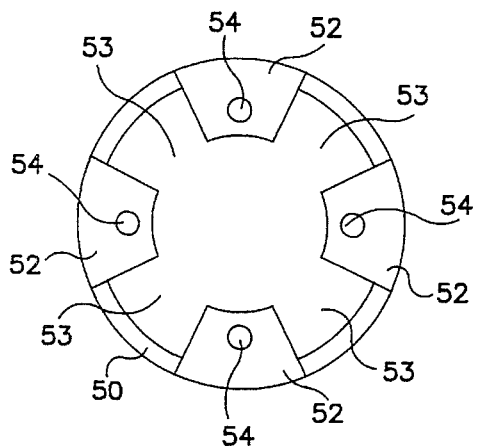
Figure 3B:
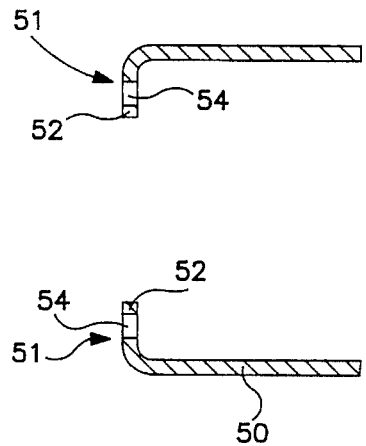

At its distal end, inner conductor 42 is electrically coupled, via spot or laser welding or the like, to tip electrode 28, shown in FIGS. 3a and 3b, respectively. Tip electrode 28 comprises a substantially cylindrical portion 50 and a forward-oriented face portion comprising a substantially annular section 51. Annular section 51 has a segmented pattern of forward-facing tabs 52 arranged radially about the lead body axis and separated from one another by a segmented pattern of spaces 53. Tabs 52 each have a through-hole 54 therein, where through-holes 54 function as steroid-elution ports, as will be hereinafter described.

In the present embodiment of the invention, a porous structure (not shown) may be sintered onto tabs 52 and over through-holes 54. The porous structure may be made by mixing a conductive material and a binder to form preferably a conductive slurry mixture as is well known in the art. Next this slurry may be deposited onto tabs 52 and sintered. Once sintered the porous structure is then preferably electroplated with a material to provide a relatively high microscopic surface area, such as platinum black in the preferred embodiment. Electroplating may be accomplished in any manner suitable to produce an electrode having a platinum black surface coating which is sufficiently durable to permit it to be implanted within a body. The porosity, together with the platinum black coating is intended to reduce capacitive resistance and polarization, as is well known in the art.

Except for the sintered distal faces of tabs 52, the remainder of tip electrode 28 is preferably insulated, thereby increasing the electrode pacing impedance by minimizing the exposed macroscopic surface area thereof. The macroscopic surface area is further minimized as a result of radially-oriented spaces 53 of the forward-facing, substantially annular portion 51 of electrode 28, since the presence of spaces 53 leaves only tabs 52 exposed to make electrical contact with endocardial tissue.

Although tip electrode 28 is segmented through four forward-facing radially-oriented tabs 52 (and a corresponding number of intervening spaces 53) it is contemplated electrode 28 may alternatively have more or fewer tabs 52 and spaces 53.

Figure 3C:
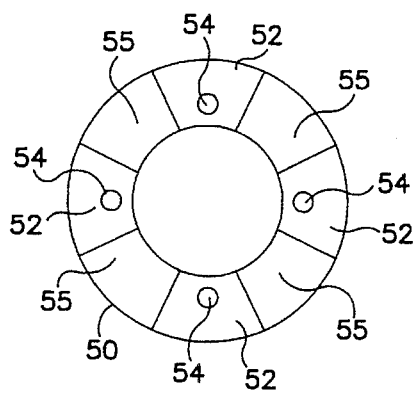
FIG. 3c is a front view of an alternate embodiment of a distal tip electrode.

In an alternative embodiment depicted in FIG. 3c, no radially-oriented space sections 53 are provided; instead, annular portion 51, although intact, is coated in radially-oriented sections with an insulative material 55, such that annular section 51 effectively comprises alternating radially-oriented conductive and non-conductive segments.

Referring again to FIGS. 2a and 2b, disposed within tip electrode 28, directly behind annular portion 51, is a washer-like polysulfone electrode shim 56 having holes therein which, in the presently disclosed embodiment of the invention, aligns with holes 54 in tabs 52 of tip electrode 28, previously described with reference to FIG. 3a. Directly behind electrode shim 56 is an annular space occupied by a similarly annular steroid monolithic controlled release device (MCRD) 58. Holes 54 and the corresponding holes in electrode shim 56, along with the porous sintered coating on tabs 52, allow steroid to elute into the tissue proximate to the distal end of lead 10. Although in the preferred embodiment a separate MCRD 58 is provided, it is also possible to provide the MCRD function to shim 56.

It is contemplated tabs 52 in annular portion 51 of electrode 28 may not be provided with steroid-elution through-holes 54. Instead, steroid elution could be accomplished though electrode shim 56 in the regions thereof which align with spaces 53 in annular section 51 of electrode 28. That is, electrode shim may itself be porous, at least in the regions which align with spaces 53, such that no steroid-elution ports 54 would be required in tabs 52.

Figure 5:
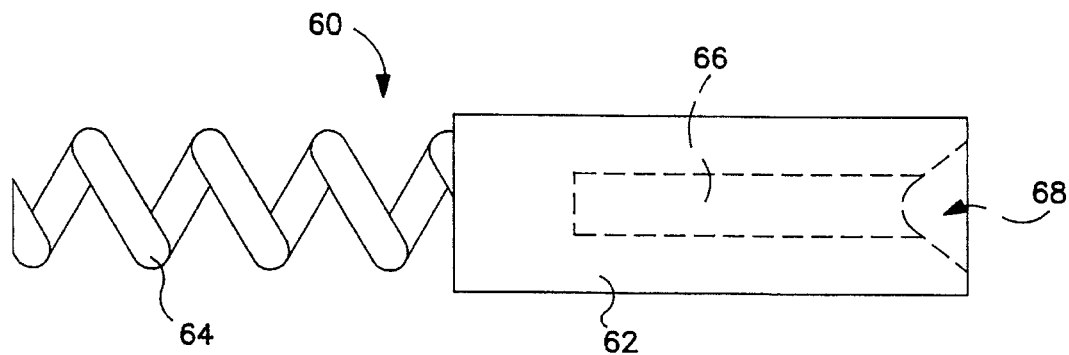

Helix assembly 60 is slidably disposed, in a piston-like fashion, in the cylindrical interior of helix sleeve 46. A greatly enlarged side view of helix assembly 60 is shown in FIG. 5. Helix assembly 60 comprises a stylet socket portion 62, which is preferably made of hard plastic, and a sharpened helix 64, the base of which may be molded into stylet socket 62 and which extends axially outward from stylet socket 62. Helix 64 is preferably made of a platinum/iridium alloy. As shown in FIGS. 2a, 2b, and 5, stylet socket 62 has an axially-oriented rectangular slot 66 formed therein, preferably having a flared opening 68 corresponding to screwdriver tip of a stylet, described below.

Helix assembly 60, best seen in FIGS. 2a, 2b and 5, is secured within helix sleeve 46 by means of a substantially cylindrical helix seal 70 which is made of molded silicone rubber. Helix seal 70 is provided with a helical lumen or channel 72 extending from front to back, through which helix 64 is able to pass, as depicted in FIGS. 2a and 2b. Helix seal 70 is further provided with a flared portion 74 around its circumference to secure seal 70 between electrode shim 56 and helix sleeve 46. When so secured, the front (distal) end of helix seal 70 defines a substantially circular, non-conductive central portion in the face of tip electrode 28.

Figure 6A:
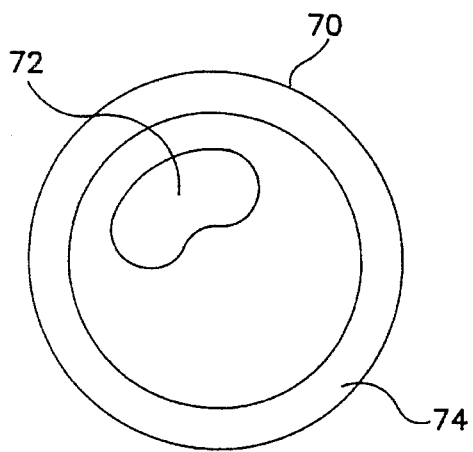
Figure 6B:
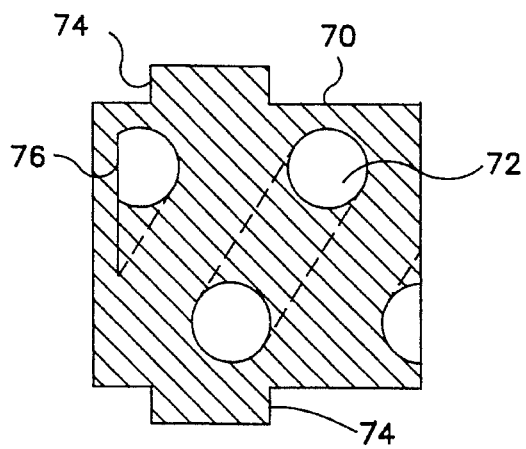

Referring to FIG. 6b, helical lumen 72 in helix seal 70 is sealed at point 76. When helix 64 is screwed into helix seal 70 from the back, helix seal 70 guides helix 64 to advance forward, such that the pointed tip of helix 64 pierces point 76 of lumen 72. When helix 64 is screwed back out, the resiliency of silicone rubber seal 70 is such that lumen 72 effectively seals itself. This self-sealing arrangement is believed to be advantageous in that it tends to prevent body fluids from entering electrode and fixation assembly 26.

TORQUE TRANSFER STYLET

Fixation assembly 26 is actuated by a torque transfer stylet 24. Torque transfer stylet 24 may be best seen in FIGS. 7–13 and has essentially three sections, a proximal straight wire section 122, a distal straight wire section 124, and an intermediate section 121 located therebetween. As seen intermediate section 121 has a length of helical torque coil 130 attached therearound.

Proximal and distal straight wire sections 122 and 124 are preferably constructed of a corrosion resistant steel wire, such as type 304 stainless steel wire, having a nominal, maximum diameter $D_1$ of approximately 0.016 inches which corresponds to the diameter of prior art stylet wires conventionally used. Proximal section 122 has a knob 174 having finger gripping members 180 formed on it to aid in transmitting torque.

Figure 8:
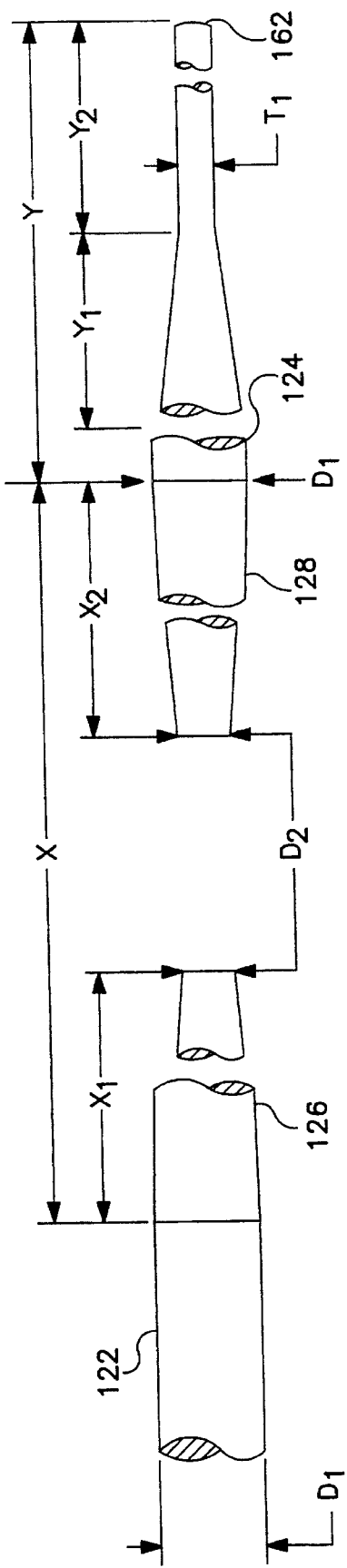
FIG. 8 is an enlarged side view of the distal end segment of the stylet showing the variations in diameter of wire coil attachment junctions of the proximal and distal straight wire sections.
Figure 11:
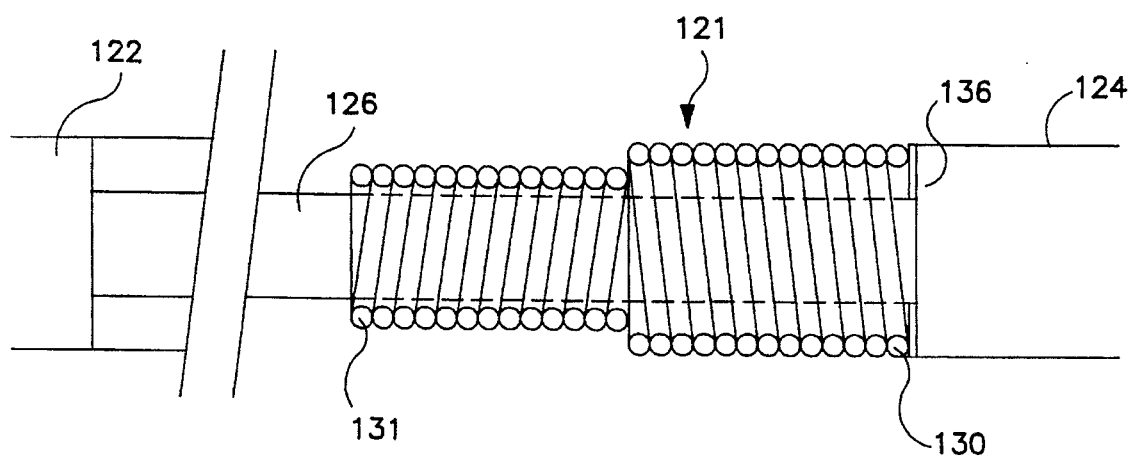
FIG. 11 is a partial sectional view of an alternate embodiment of a stylet according to the present invention.

Distal section 124 of torque transfer stylet 24, as best seen in FIG. 8, has a length Y ending with tip 162. Length Y is preferably between 0.160 and 0.180 inches. Tip 162 has a length $Y_2$ of typically 0.13 inches, and a tapered length $Y_1$ of 0.03 inches, typically. Tip 162 may have a radius of 0.008 inches and a thickness $T_1$ between its flattened sides in region $Y_2$ of 0.008 inches. Although tip 162 is depicted as a screwdriver, it may also be configured to conform to a variety of attachment mechanisms or conventions, e.g. TORX, hexagonal socket or Phillips driver shapes, shaped in slot 66 of helix assembly 60.

Proximal and distal sections 122 and 124 are depicted in FIG. 8 with proximal and distal, tapered portions 126 and 128, respectively, having lengths denoted as $X_1$ and $X_2$, respectively, to facilitate attachment within and to helical torque coil 130 (not depicted in FIG. 8 for clarity.) The reduced diameter, proximal and distal portions 126 and 128 are tapered down to a reduced diameter $D_2$ of about 0.008 inches. Moreover, these portions may or may not be provided in any appreciable length or degree, as the length of each may reflect a wire drawing or grinding transition zone dependent on the method and equipment employed to draw or grind ends of proximal and distal wire sections 122 and 124 down to reduced diameter $D_2$ from the regular diameter $D_1$.

As depicted in FIG. 7 helical torque coil 130 extends over length X of torque transfer stylet 24. The exact dimension X may depend on the length of a J-shape pre-formed in the atrial endocardial lead the stylet is to be used in. For example, length X may be on the order of about 10 cm or 4.0 inches. The wire of helical torque coil 130 is preferably a 304 stainless steel of a diameter in the range of 0.003 inches and has an inside coil diameter approximating reduced diameter $D_2$ or about 0.008 inches.

Figure 12:
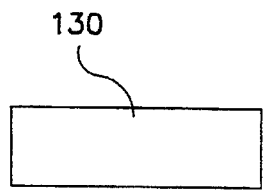
FIGS. 12 and 13 are sectional views of alternate embodiments of the helical wire torque coil used in a lead system of the present invention.

Helical torque coil 130 as seen in FIG. 12 preferably consists of a pair of counter-wound coils 130 and 131 which extend between distal section 124 and proximal section 122 (although only a portion of coils 130, 131 are shown for clarity.) An acceptable torque coil 130 may be one such as disclosed in the U.S. Pat. No. 5,165,421 to Fleischhacker discussed above. Although a pair of counter-wound coils is preferred for torque coil, it should be understood a single coiled wire may also be used. Coils 130, 131 may be fastened to the torque transfer stylet 24 in any acceptable fashion, preferably through use of a brazing alloy 136.

As shown in the partial cross section drawing of FIG. 9, portion 126 of proximal wire section 122 may be formed with a tapered sub-portion 123 terminating in relatively straight sub-portion 125 of length $X_1'$. Portion 126 is fitted within lumen 132 defined by the inner diameter of helical torque coil 130 such that wire coil lumen 132 is expanded as the end-most turns of end section 134 of helical torque coil 130 are forced onto tapered sub-portion 123 of length $X_1''$. The various dimensions including lengths $X_1$, $X_1'$, $X_1''$ depicted in FIG. 10 (as well as the other figures) are arbitrary in relation to the stylet wire diameters for ease of illustration and therefore may be relatively shorter or longer in practice.

End section 134 of helical torque coil 130 extending over tapered sub-portion 123 and part of straight sub-portion 125 is brazed to the underlying surface of portion 126 as shown by darkened brazing alloy 136. The diameter $D_1$ of the portion of torque transfer stylet 24 having helical torque coil 130 is restored after brazing by grinding down any expanded turns of end section 134 of helical torque coil 130 and any excess brazing alloy 136. In this fashion, a secure bond of end section 134 of helical torque coil 130 and straight wire section 122 is obtained while maintaining uniform outer diameter $D_1$.

Diameter $D_2$ of straight wire sub-portion 125 is smaller than inner diameter defining wire coil lumen 132. In the example described above, diameter $D_2$ may be reduced 0.008 inches from the 0.016 inch diameter $D_1$ and thus to 0.008 inches to allow the 0.003 inch wire diameter helical torque coil 130 to be wound thereon with a slight gap, in the present embodiment as illustrated 0.001 inches. This gap allows helical torque coil 130 to stretch longitudinally and flex laterally and bear against sub-portion 125 when torque transfer stylet 24 is bent in the length of helical torque coil 130. This action reinforces the junction of attachment from fracture, and is desirable particularly in the more proximal attachment of straight wire section 122 with helical torque coil 130 which may be subjected to greater stress. For example, when torque transfer stylet 24 is inserted into the lumen of connector pin 18 of a lead, length X of helical torque coil 130 may be bent laterally as torque transfer stylet 24 is inserted, applying force on the junction of attachment in the length $X_1$. Distal straight wire section 124 is shorter and easier to insert into lumen of connector pin 18 without bending and stressing the junction of attachment. Of course helical torque coil 130 may also be directly attached to intermediate section 121 as well as directly wrapped about intermediate section 121 without departing from the scope of the present invention.

FIG. 10 depicts an alternate attachment which may be more useful in the junction of attachment of distal section 124 with helical torque coil 130 in portion 128. In this embodiment, portion 128 is substantially straight, rather than tapered, although a minor unintended taper may exist due to wire forming and fabrication limitations at the junction with distal section 124. Brazing alloy 136 fills the gap between inner diameter lumen 132 of helical torque coil 130 and diameter $D_2$ as well as the gaps between adjacent turns of helical torque coil 130 over entire junction length $X_2$. Again, excess brazing alloy 132 is ground away to maintain uniform outer diameter $D_1$.

As mentioned above, portions 126 and 128 may take any of the forms depicted in the FIGS. and may be used in any combination in any given stylet following the construction techniques described above. Other techniques of attaching helical torque coil 130 around first or second sections 126 and 128, e.g. by welding or bonding the contacting coil turns to the surface of the reduced diameter portion, may also be employed.

Figure 13:
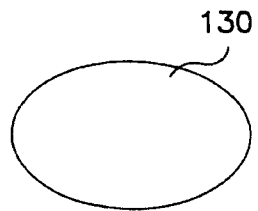
Figure 14A:
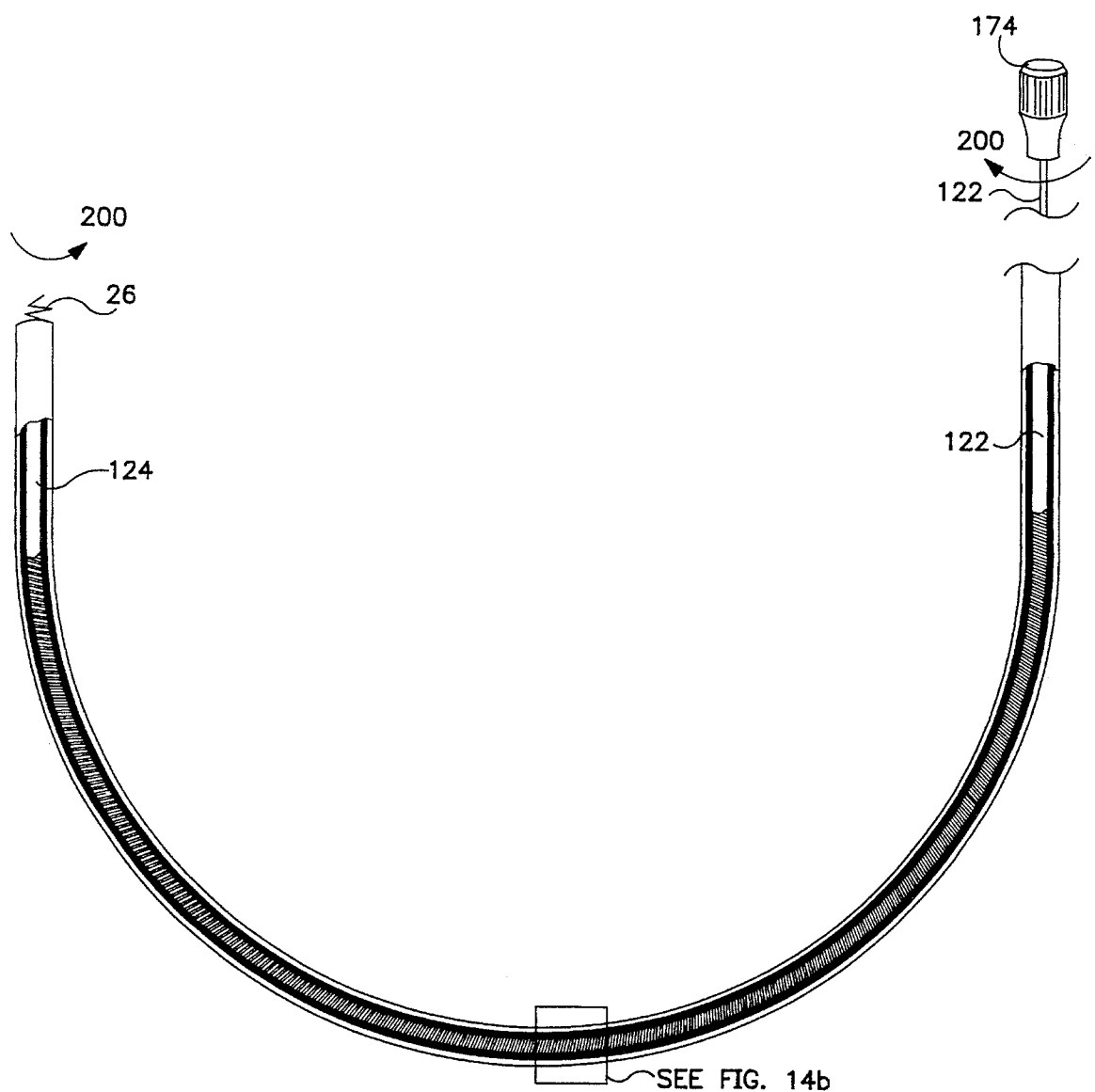
FIG. 14 depicts the torque stylet used to activate a helix in a bent lead.
Figure 14B:
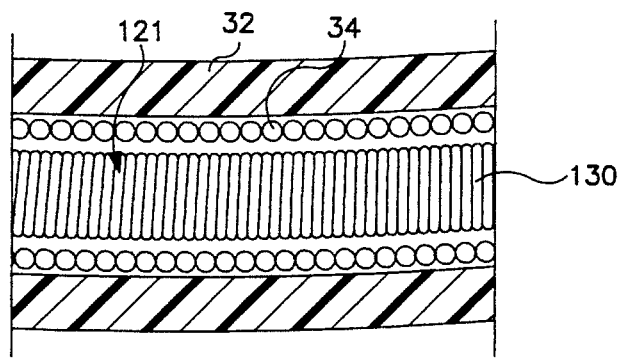

FIGS. 13 and 14 are cross sectional views of alternate embodiments of coils which may be used within the helical torque coil 130 of the present invention. Such various geometries may be used to tailor the specific torque transfer and stylet stiffness characteristics desired. As seen in FIG. 13 a helical torque coil 130 used in a stylet of the present invention may feature a non-circular rectangular cross section. As seen in FIG. 14 a helical coil 30 used in a stylet of the present invention may further feature a non-circular elliptical cross section. Further details and examples of the use of various cross sectional geometries to accomplish torque transfer through a helical coil may be found in the co-pending application of Karel Smits U.S. patent application Ser. No. 08/043,885 filed Apr. 7, 1993 and entitled "Conductor Coil with Specific Ratio of Torque to Bending Stiffness."

Figure 15:
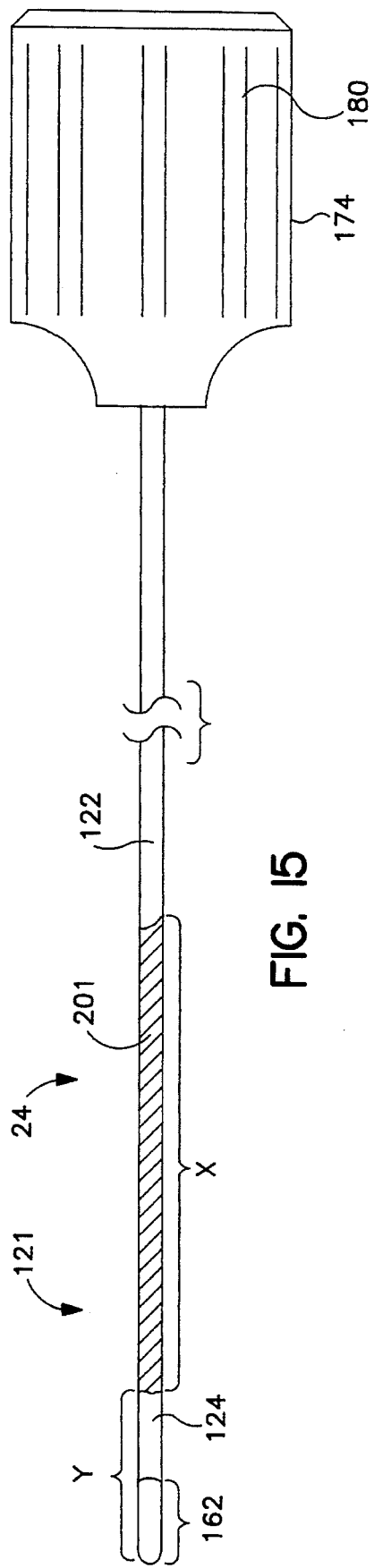
FIG. 15 is a side view of an alternate embodiment of a stylet used in conjunction with the lead from FIG. 1.

FIG. 15 illustrates the torque transfer stylet 24 of the present invention disposed through a lead 26. As seen rotation of knob 180 in direction 200 causes distal end of torque transfer stylet 24 and thus helix 64 to also rotate in the same coaxial direction (it should be noted it appears to be in the opposite direction since the lead is bent 180 degrees). Due to the increased flexibility of the torque transfer stylet 24 along intermediate portion 124 along with the provision of torque coil 130 stylet 24 readily rotates about its longitudinal axis without bending a causing the distal end of the lead 26 to be displaced.

Figure 16:
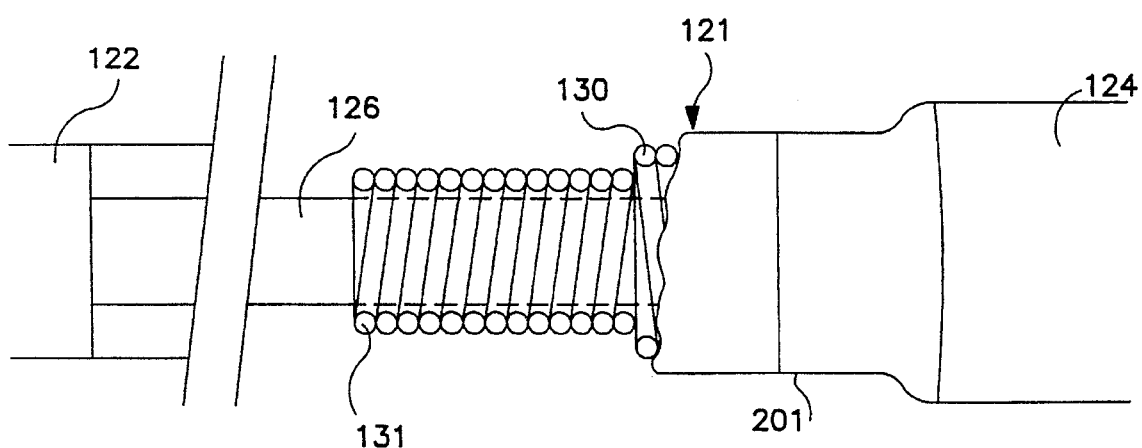
FIG. 16 is a partial sectional view of the alternate embodiment of a stylet depicted in FIG. 15

A further alternate embodiment of the present invention may be seen in FIGS. 15 and 16. In particular FIG. 15 is a side view of this additional alternate embodiment. As seen this embodiment is identical to that shown in FIG. 7a and described above but for the addition of sleeve 201. FIG. 16 is a partial sectional view of the alternate embodiment of a stylet depicted in FIG. 15. As seen sleeve 201 wraps around and cover torque coils 130, 131 (although shown only partially covering these coils for the sake of clarity.) Sleeve 201 acts as a lubricous solid layer to facilitate rotation of stylet within lead even when deflected (as best seen in FIG. 14) Specifically sleeve 201 prevents torque coil from directly contacting lead coil. Sleeve 201 also facilitates sliding of lead 86 over stylet 2 in a longitudinal direction. Sleeve 201 is preferably constructed from a hard, high elastic modulus, polymeric material, such as polyimide. Sleeve 201 may also be constructed from a metal, such as stainless steel or Nitinol.

INTRODUCTION AND FIXATION OF THE MEDICAL ELECTRICAL LEAD WITH THE TORQUE TRANSFER STYLET

Transvenous implantation of lead 10 may be accomplished using conventional lead introduction techniques. During the implantation procedure, torque transfer stylet 24 is used to provide stiffness to lead body 12, facilitating manipulation of lead 10 through the patient's venous system. Helix assembly 60 is maintained in its most retracted position until the distal end of electrode and fixation assembly is brought into contact with the desired endocardial stimulation site. Since helix assembly 60 is contained completely within the electrode and fixation assembly, it is prevented from damaging tissue as lead 10 is advanced through the venous system.

Once the desired electrode positioning is achieved, torque transfer stylet 24 is rotated in the appropriate direction to cause helix 64 to advance through helical channel 72 within helix seal 70, eventually piercing sealed portion 76 at the distal end of helical channel 72. Continued rotation of helix 64 will cause further advancement, so that helix 64 pierces and engages the endocardial tissue. In this way, electrode and fixation assembly 26, and in particular, tip electrode 28, is secured in contact with the desired stimulation site. The porous sintered coating on tabs 52 of electrode 28 allows steroid from MCRD 58 to elute from the lead at the location of the lead/tissue interface. Thus, the full benefits associated with steroid elution, well documented in the prior art, are realized, and secure fixation of the lead at the stimulation site is achieved.

A further advantage of the present invention is that the fixation mechanism of lead 10 can be released, without significant damage to the cardiac tissue, by simply rotating torque transfer stylet 24 in the opposite direction. Such retraction of helix 64 may be desired, for example, if it is necessary to relocate the lead.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

It should be further understood, of course, that the foregoing disclosure relates only to the best mode known to the inventors of many possible modes of practicing the torque transfer stylet of the present invention and that numerous modifications may be made therein without departing from the spirit and scope of the invention as set forth in the appended claims, including the use of the stylet with other various types of extendable screw leads. Such modifications may include substituting elements or components which perform substantially the same function in substantially the same way to achieve substantially the same result for those described herein.

What is claimed is:

1. A body implantable lead system comprising:

a lead for electrically communicating with a tissue of a body, said lead having a conductor having a proximal end and a distal end, said conductor having a lumen, said conductor covered between said proximal end and said distal end by an insulative sheath, a fixation helix positioned at said distal end of said conductor, said fixation helix having a proximal end and a distal end, said proximal end of said fixation helix having means for receiving a torque;

a stylet disposed through said lumen of said lead, said stylet having a distal section, an intermediate section and a proximal section;

said distal section having a first diameter, said distal section having means for transmitting a torque to said means for receiving a torque of said proximal end of said fixation helix;

said intermediate section being attached to said distal section, said intermediate section having a second diameter smaller than said first diameter, said intermediate section further having a torque coil, said torque coil being attached to said intermediate section; and said proximal section being attached to said intermediate section.

2. The body implantable lead system of claim 1 further comprising said intermediate section having an intermediate section diameter, said intermediate section diameter being no greater than said first section diameter.

3. The body implantable lead system of claim 1 wherein said means for receiving a torque comprises a slot.

4. The body implantable lead system of claim 1 wherein said means for transmitting a torque comprise a screwdriver.

5. The body implantable lead system of claim 1 wherein between said intermediate section and said torque coil attached to said intermediate section there is a gap.

6. The body implantable lead system of claim 1 wherein said torque coil is directly attached to said intermediate section.

7. The body implantable lead system of claim 1 wherein said torque coil is directly wrapped about said intermediate section.

8. The body implantable lead system of claim 1 wherein said torque coil is fashioned from a wire, said wire having a circular cross-section.

9. The body implantable lead system of claim 1 wherein said torque coil comprises a first helical coil and a second helical coil.

10. The body implantable lead system of claim 9 wherein said first helical coil is wound in a first direction and said second helical coil is wound in a second direction.

11. A stylet comprising:

an elongated stylet wire having a distal section, an intermediate section and a proximal section, said proximal section having a knob mounted thereto to aid in transmitting torque, said intermediate section having a first diameter, said distal section having a second diameter, said first diameter being smaller than said second diameter;

a torque coil positioned about said intermediate section to form a torque transfer section, said torque transfer section having a third diameter, said torque coil fixedly attached to said stylet wire, wherein said third diameter is no greater than said second diameter.

12. The stylet of claim 11 wherein said torque coil has a center lumen of a fourth diameter, said fourth diameter being greater than said second diameter.

13. The stylet of claim 11 wherein between said intermediate section and said torque coil attached to said intermediate section there is a gap.

14. The stylet of claim 11 wherein said torque coil is directly attached to said intermediate section.

15. The stylet of claim 11 wherein said torque coil is directly wrapped about said intermediate section.

16. The stylet of claim 11 wherein said torque coil is fashioned from a wire.

17. The stylet of claim 16 wherein said wire having a circular cross-section.

18. The stylet of claim 11 further comprising a sleeve of a high elastic modulus, polymeric material positioned over said torque coil.

19. The stylet of claim 11 wherein said torque coil comprises a first helical coil and a second helical coil.

20. The stylet of claim 19 wherein said first helical coil is wound in a first direction and said second helical coil is wound in a second direction.

21. A body implantable lead system comprising:

a lead for electrically communicating with a tissue of a body, said lead having a conductor having a proximal end and a distal end, said conductor covered between said proximal end and said distal end by an insulative sheath, a fixation helix positioned at said distal end of said conductor, said fixation helix having a proximal end and a distal end, said proximal end of said fixation helix having means for receiving a torque;

a stylet, said stylet introduced into said lead, said stylet comprising a knob and a stylet wire, said stylet wire having a first section, an intermediate section and a third section, said first section having a first diameter, said intermediate section having a second diameter, a torque coil positioned around said intermediate section, said torque coil attached at a first end to said stylet wire and attached at said second end to said stylet wire, said torque coil having a diameter no greater than said first diameter.

22. The body implantable lead system of claim 21 wherein said torque coil comprises a first helical coil and a second helical coil.

23. The body implantable lead system of claim 21 wherein said first helical coil is wound in a first direction and said second helical coil is wound in a second direction.

24. The body implantable lead system of claim 23 wherein said first direction of said first helical coil is opposite said second direction of said second helical coil.

25. The body implantable lead system of claim 21 wherein said first helical coil has a diameter less than said first diameter of said distal section.

26. The body implantable lead system of claim 21 wherein said second helical coil has a diameter greater than said second diameter of said intermediate section.

27. The body implantable lead system of claim 21 wherein said second helical coil is located around said first helical coil.

28. The body implantable lead system of claim 21 wherein said first section further comprises means for transmitting a torque to said means for receiving a torque of said proximal end of said fixation helix.

29. The body implantable lead system of claim 22 further comprising a sleeve of a high elastic modulus, polymeric material positioned over said torque coil.

30. The body implantable lead system of claim 21 wherein said high elastic modulus, polymeric material is polyamide.

* * * * *